United States Patent [19]
Fry

[11] Patent Number: 5,520,175
[45] Date of Patent: May 28, 1996

[54] ENDOTRACHEAL TUBE WITH SUCTIONING MEANS

[76] Inventor: William R. Fry, 15 Abrook, Colorado Springs, Colo. 80906

[21] Appl. No.: 445,683

[22] Filed: May 22, 1995

[51] Int. Cl.$^6$ ............................................. A61M 16/00
[52] U.S. Cl. ........................... 128/207.15; 128/207.14
[58] Field of Search ........................ 128/207.14, 207.15; 604/102

[56] References Cited

U.S. PATENT DOCUMENTS

| | | | |
|---|---|---|---|
| 4,305,392 | 12/1981 | Chester | 128/276 |
| 4,327,721 | 5/1982 | Goldin et al. | 128/207.15 |
| 4,502,482 | 3/1985 | DeLuccia et al. | 128/207.15 |
| 4,637,389 | 1/1987 | Heyden | 128/207.15 |
| 4,840,173 | 6/1989 | Porter, III | 128/207.15 |
| 4,979,505 | 12/1990 | Cox | 128/207.15 |
| 5,067,497 | 11/1991 | Greear et al. | 128/207.15 |
| 5,143,062 | 9/1992 | Peckham | 128/207.14 |
| 5,201,310 | 4/1993 | Turnbull | 128/207.15 |
| 5,241,956 | 9/1993 | Brain | 128/207.15 |
| 5,311,864 | 5/1994 | Huerta | 128/207.15 |

*Primary Examiner*—Aaron J. Lewis
*Attorney, Agent, or Firm*—Gifford, Krass, Groh, Sprinkle, Patmore, Anderson & Citkowski

[57] ABSTRACT

An improved endotracheal tube provides an inflatable cuff having a concavely shaped superior surface forming a collection basin and means to facilitate accurate suctioning of the basin while the tube is in position. In the preferred embodiment the means to facilitate accurate suctioning of the collection basin takes the form of a guide wire having one end attached within the basin and the other end terminating freely outside the body of the patient, thus enabling a suction catheter to be slideably moved along the guide wire and into the basin to remove substances collected therein. The preferred embodiment further includes means to releasably secure the free end of the guide wire when not in use. Alternative means to facilitate accurate suctioning include the provision of a separate passageway having a first end external to the body of the patient for connection to a suctioning means and a second end terminating within the basin. This separate passageway may either be bonded along at least a portion of the ventilation tube or provided as a lumen extending within at least a portion of the wall of the ventilation tube.

12 Claims, 1 Drawing Sheet

ENDOTRACHEAL TUBE WITH SUCTIONING MEANS

FIELD OF THE INVENTION

The present invention relates generally to endotracheal tubes of the type including an inflatable balloon or cuff-type seal and, more particularly, to such a tube wherein the cuff forms a collection basin when inflated, and further including means to guide a suction catheter into the basin for removal of substances collected therein.

BACKGROUND OF THE INVENTION

During anesthesia and in intensive care situations, it is standard practice to intubate the patient with a tube, introduced into the trachea, to facilitate pulmonary ventilation. Modern tracheal tubes now typically include an inflatable balloon or cuff near their distal end to occlude the air passageway and maintain respiration, and, secondarily, to provide barrier against aspirated substances. The inflatable cuff on a typical commercially available endotracheal tube is in the form of an oval or sphere-shaped balloon which permits these secretions to pool around the superior surface and, in some circumstances, pass by the balloon and into the tracheobronchial tree. While it is standard protocol to attempt suctioning of this surface, it is awkward and, done blindly, may result in the incorrect suctioning of the pharynx. In any case, the procedure is not effective in the ICU setting.

To ensure that proper suctioning occurs in an around the superior surface of the inflatable cuff, it is known in the art to provide a separate tube or lumen directed into this area. For example, U.S. Pat. No. 5,067,497 "Intubation Device with Adjustable Suction Means Above the Cuff" discloses a suction tube that runs along the main tube body, which is fixed with respect to the main tube except for an adjustable portion near the cuff to improve suctioning above a standard inflatable balloon. U.S. Pat. No. 5,143,062 "Endotracheal Tube Having Irrigation Means" also includes a suction inlet just above the proximal portion of the inflatable cuff.

U.S. Pat. No. 5,201,310 "Medico-Surgical Tube with Sealing Cuff and a Suction Lumen at the Top of the Cuff" includes a suction lumen extending along the tube and an opening through a suction aperture immediately adjacent the upper, proximal end of the cuff. The inflatable cuff is attached to the external surface of the tube by collars. The proximal collar is inverted within the inflatable portions of the cuff so that it does not extend beyond the inflatable portion and so that the maximum amount of secretions can be removed through the suction aperture.

U.S. Pat. No. 5,311,864, "Tracheas Evacuation and Transmittal Tube," shows a suction lumen disposed along the ramped portion of the inflatable balloon at its proximal end. U.S. Pat. No. 4,305,392 "Endotracheal Tube with Suction Device" includes an inflatable cuff and a suction chamber adjacent the upper side of the cuff. The suction chamber is in the shape of a bulge having four ports equally spaced around the periphery and facing upwardly. U.S. Pat. No. 4,502,482 "Endotracheal Tube Complex" includes a suction tube which fits into the main tube body to aspirate fluids from the lungs.

U.S. Pat. No. 4,637,389 "Tubular Device for Intubation" includes an expansible channel along the length of the tracheal tube with perforations into which a suction catheter may be guided for the removal and secretions and other substances which might accumulate around the tube. U.S. Pat. No. 4,840,173 "Endotracheal Tube Combination" includes combined dual passages to provide a ventilation tube and a suction tube. The suction passage terminates at the cuff with openings into the suction passage for secretions that might pool around the cuff.

Whether provided in the form of a separate lumen, tube, or a cavity to accept a separate tube, these references provide means for suctioning in and around a more or less conventional oval-shaped balloon, and although these references solve problems associated with the area in which suctioning should be carried out, they do not solve problems associated with effectively collecting aspirated substances in the first place which, if addressed, might reduce the frequency with which suctioning is required, perhaps avoiding the need for suctioning in critical care situations, and minimizing patient discomfort.

U.S. Pat. No. 4,979,505 to Cox discloses a low-pressure inflatable cuff for tracheal tube use taking the form of first and second paraboloid portions which are inverted with respect to one another to approximate an hourglass configuration. This shape is primarily designed to ameliorate the complications of the constant pressure of the inflatable cuff and decrease injury associated with prolonged intubation. Should aspiration occur, however, the fluids or particulate matter are trapped in the open reservoir created around the tube by the upper paraboloid shaped cuff, which has its open end oriented toward the larynx. Thus, this reference addresses the shape of an inflatable cuff on a tracheal tube to more effectively collect aspirated substances. However, two cuffs are required in this design, because the lower paraboloid is designed specifically for respiratory control, requiring the upper paraboloid to protect the pulmonary tree against aspiration and secretions. Moreover, while this reference makes no reference to the suctioning of fluids and particulate matter trapped within the reservoir of the upper paraboloid, it can be assumed that standard suctioning procedures are intended, in which case the problems associated with blindly positioning the suctioning tube in the correct spaces are neither addressed nor eliminated by this cuff design. As such, there remains a need for an endotracheal tube including a single inflatable cuff forming a collection basin in combination with means to provide suctioning precisely within this basin for an effective removal of substances collected therein.

SUMMARY OF THE INVENTION

The present invention improves upon existing endotracheal tubes of type including an inflatable cuff by providing a cuff that inflates to form a convexly shaped superior surface which functions to collect secretions and aspirated substances. In combination, the improved endotracheal tube integrates means to facilitate accurate suctioning of the collection basin while the tube is in position. In the preferred embodiment the means to facilitate accurate suctioning of the collection basin takes the form of a guide wire having one end attached within the basin and the other end terminating freely outside the body of the patient, thus enabling a suction catheter to be slideably moved along the guide wire and into the basin to remove substances collected therein. The preferred embodiment further includes means to releasably secure the free end of the guide wire when not in use.

Structurally, the inventive endotracheal tube comprises a flexible ventilation tube having a proximal end adapted for connection to a ventilator and a distal end terminating within a patient's trachea, with the inflatable balloon cuff being attached near the distal end of the ventilation tube so as to provide a seal against the inner wall of the trachea during use. A separate tube or lumen is provided to inflate the cuff and means are further provided to facilitate accurate suctioning of the collection basin while the tube is in position with the cuff inflated to form the concave cup shape on it superior surface.

Alternatives are possible within the scope of the invention to facilitate accurate suctioning, including means to guide a suction catheter directly into the basin to remove substances collected therein. While the preferred embodiment provides a guide wire for this purpose, alternatively a separate passageway may be included having a first end external to the body of the patient for connection to a suctioning means and a second end terminating within the basin. This separate passageway may either be bonded along at least a portion of the ventilation tube or provided as a lumen extending within at least a portion of the wall of the ventilation tube.

DETAILED DESCRIPTION OF THE PREFERRED EMBODIMENT

Figure 1:
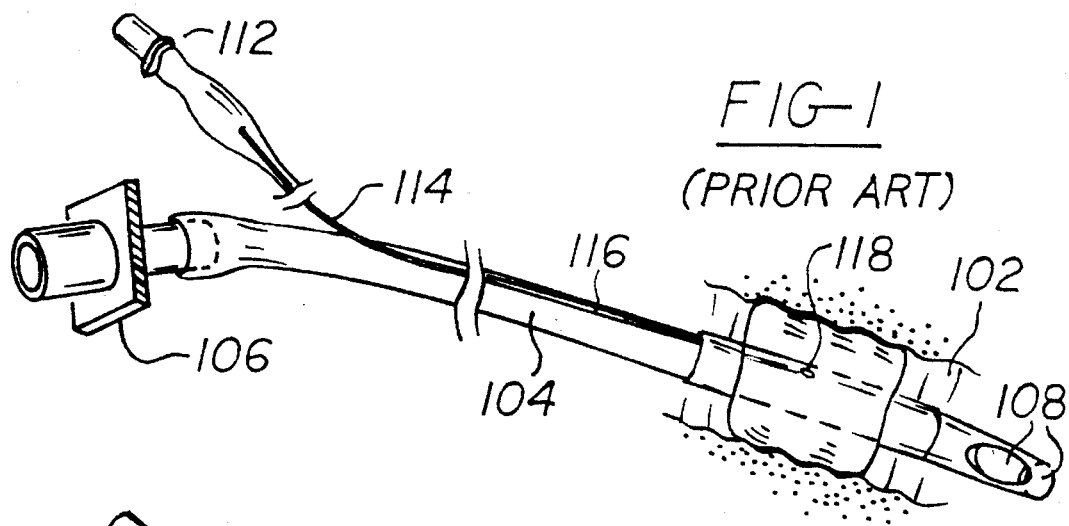
FIG. 1 is a drawing which shows a prior art endotracheal tube of the type having an inflatable cuff which seals against a portion of the inner wall of the trachea.

FIG. 1 is a drawing which illustrates a typical prior art endotracheal tube of the type having an inflatable balloon or cuff which seals against the inner wall of the trachea. This device includes a main tube 104 having a proximal end which extends out of the body of the patient, typically including an adapter 106 facilitate connection to standard ventilator. The main tube 104 has, at its distal end, one or more openings 108 to facilitate the passage of gases into and out of the patient's respiratory system. This main tube 104 is typically composed of a pliable clear plastic material, and tubes of this type may be introduced orally, nasally, or via incision.

An inflatable cuff 110 is provided proximate to the distal end of the main tube body 104. The cuff is inflated through a tube 114, which may be bonded lengthwise alongside the main tube 104, or, as shown at 116, may be formed internal to the wall of the main tube as a separate lumen. The proximal end of the tube 114 typically includes a port 112 to facilitate inflation, either manually, or more usually, through the use of a syringe. The distal end of the tube 114 terminates at a point 118, where an aperture is formed through the tube wall and into the volume defined by the cuff, thus facilitating inflation. In an ideal situation, the cuff 110 is inflated just enough to provide a gas and liquid-tight seal against at least a portion of the inner wall of the trachea 102, but not overinflated result in necrosis of the surrounding tissue.

A problem arises with the use of this prior art device shown in FIG. 1, in that oropharyngeal and refluxed gastric secretions gain access to the trachea since the introduction of the endotracheal tube renders the vocal chords incapable of closing, which would otherwise protect the tracheal bronchial tree from such substances. These prior-art endotracheal tubes utilize an oval or sphere-shaped balloon such as that shown in FIG. 1 at 110, which allows these secretions to pool around in the area 120 and, particularly in the case of improperly low inflation, these substances may travel between the outer surface of the cuff and inner wall of the trachea and find their way into the tracheobronchial tree, causing infection or more serious problems, including pneumonia. While it is common to attempt suctioning of this volume 120, the procedure can be awkward and, if the individual performing the suctioning is not skilled, the suction tube may be incorrectly placed into the larynx instead of the trachea. In any event, suctioning in conjunction with the prior-art tube must be done blindly, leading to a haphazard procedure which may not be carried out effectively in an ICU setting.

Figure 2A:
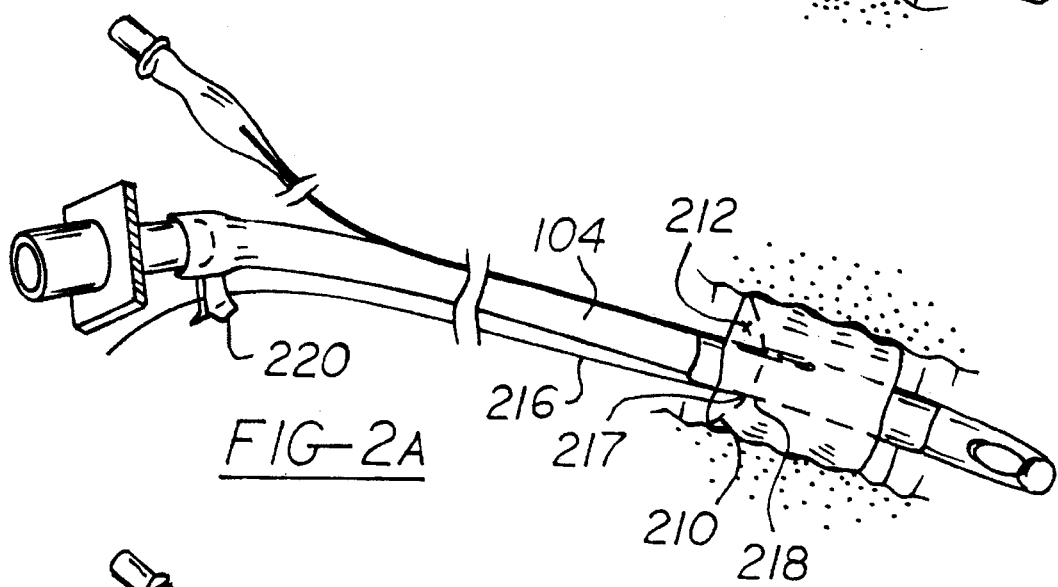
FIG. 2A is an improved endotracheal tube constructed in accordance with this invention including a collection basin and guide wire with one end secured within this basin and the second, free end of the wire removably secured outside the body of the patient.
Figure 2B:
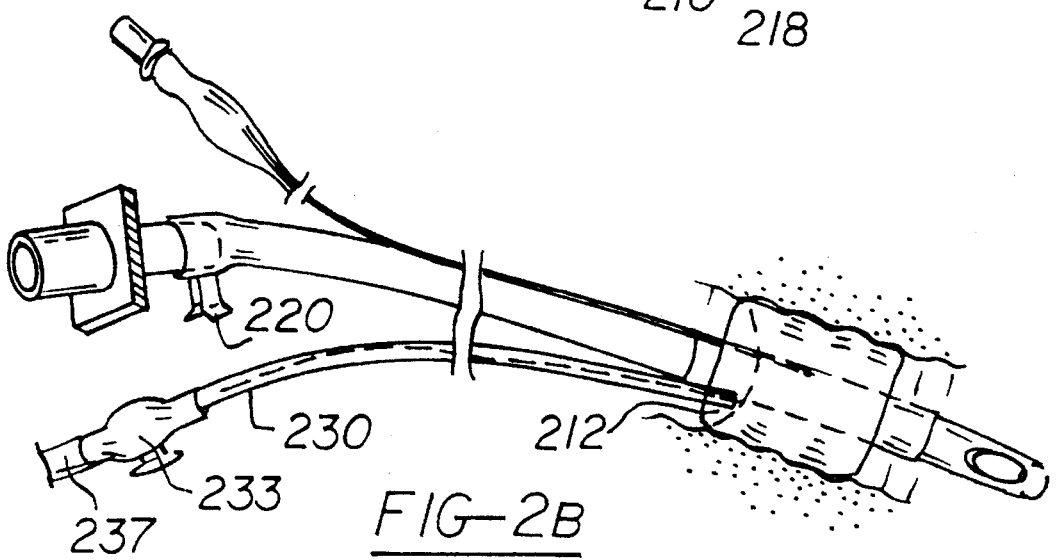
FIG. 2B is a drawing of the improved endotracheal tube according to FIG. 2A wherein a suction tube has been monorailed onto the guide wire and accurately placed within the basin to remove secretions and aspirated substances collected therein.

To facilitate the collection and removal of secretions above the active airway in the intubated patient, the present invention provides two distinct differences from the conventionally used endotracheal tube. Making reference to FIG. 2A, the first improvement concerns the shape of the superior surface of the single balloon cuff. According to the invention, this surface 210, rather than being oval-shaped or uncontrolled, is intentionally designed to take on a concave cup-shape upon inflation, resulting in the formation of a collection basin 212 facing the defunctionalized or "inactive" airway above the inflated cuff. As secretions accumulate within this basin, the edge of the cuff is also preferably forced by the weight of the secretions against the wall of the trachea, thus functioning as a flap-type valve to further occlude the trachea and protect against the aspiration of oropharyngeal or gastrointestinal secretions, should they occur. Although FIGS. 2A and 2B show a slightly concaved superior surface 210 it should be recognized that the degree of concavity may be more or less pronounced so long as a collection basin is formed.

The second improvement includes the use of a guide wire 216, which has a distal end 218 attached to a portion of the wall of the main tube 104, and which emerges at a point 217 proximate to the bottom of the collection basin 212. The guide wire 216 travels freely alongside the main tube 104 and out of the body of the patient, where it may conveniently be removably secured when not in use to the main tube body, for example using the optional clip 220 shown in FIG. 2A. It will be recognized that clips other than the one depicted in the figure may be alternatively used for this purpose.

The guide wire 216 allows the accurate passage of a suction catheter into the inactive airway for the removal of secretions within this dead space. Since, in the preferred embodiment, the guide wire emerges from the wall of the main tube precisely near the bottom of the collection basin, when the suction catheter is monorailed over this guide wire, its distal end terminates precisely within the bottom of the basin, thereby enabling an efficient and effective suctioning to be performed without guesswork. Typically the suction tube 230 is connected to an air vent 233 which further connects to suction tubing 237 to a wall-mounted suctioning apparatus, the suction tube and associated valves and connections being of conventional design, and not forming part of this invention.

Although the preferred embodiment shows the use of a guide wire on which a conventionally provided suction catheter may be slidable positioned, other means for accurately suctioning the basin formed by the improved cuff may alternatively be provided. For example, separate conduits attached to the outer wall of the main tube 104, or lumens disposed longitudinally within the wall of the main tube may alternatively be provided, in which case an aperture formed on the distal end of such passageways would, according to this invention, necessarily be positioned in the same vicinity as that wherein the guide wire of the preferred embodiment emerges. For example, tubular assemblies of the type disclosed in U.S. Pat. Nos. 5,067,497 or 5,201,310, 4,840,173 may be used in conjunction with the cuff design of the present invention, or, as a further alterative, the catheter guiding mechanism disclosed in U.S. Pat. No. 4,637,389 may optionally be employed.

The use of a guide wire is preferred, however, since its use should result in more economical manufacture and less imposing when not in use as compared to a permanently installed suction tube and connectors.

Having thus described my invention, I claim:

1. An endotracheal tube, comprising:

a flexible ventilation tube having a proximal end adapted for connection to a ventilator and a distal end terminating within a patient's trachea;

an inflatable balloon cuff attached near the distal end of the ventilation tube to provide a seal against an inner wall of a trachea, the cuff including a convexly shaped superior surface facing the proximal end which, when inflated, forms a collection basin;

means to inflate the cuff; and means integral to the endotracheal tube to facilitate accurate suctioning of the collection basin while the tube is in position.

2. The endotracheal tube as set forth in claim 1, the means integral to the endotracheal tube to facilitate accurate suctioning including means to guide a suction catheter directly into the basin to remove substances collected therein.

3. The endotracheal tube as set forth in claim 2, the means to guide a suction catheter directly into the basin taking the form of a guide wire having one end attached within the basin and the other end terminating freely outside the body of the patient, enabling the suction catheter to be slideably moved thereon and into the basin.

4. The improved endotracheal tube as set forth in claim 3, further including means to releasably secure the free end of the guide wire when not in use.

5. The endotracheal tube as set forth in claim 1, the means integral to the endotracheal tube to facilitate accurate suctioning including a separate passageway having a first end external to a body of a patient for connection to a suctioning means and a second end terminating within the basin.

6. The endotracheal tube as set forth in claim 5, the separate passageway being bonded along at least a portion of the ventilation tube.

7. The endotracheal tube as set forth in claim 5, the separate passageway being a lumen extending within at least a portion of the wall of the ventilation tube.

8. In an endotracheal tube including an inflatable cuff which seals against an inner wall of a trachea, the improvement comprising:

a convexly shaped superior surface on cuff when inflated, thereby forming a collection basin; and means integral to the endotracheal tube to facilitate accurate suctioning of the collection basin while the tube is in position.

9. The improved endotracheal tube of claim 8, the means integral to the endotracheal tube to facilitate accurate suctioning of the collection basin including:

a guide wire having one end attached within the basin and the other end terminating freely outside a body of a patient, thus enabling a hollow suction catheter to be placed thereon and slidingly moved into the basin to remove substances collected therein.

10. The improved endotracheal tube of claim 9, further including means no releasably secure the free end of the guide wire when not in use.

11. An endotracheal tube, comprising:

a primary flexible hollow tube having proximal and distal ends, the proximal end extending out of a body of a patient and being adapted for attachment to ventilation means, the length of the primary tube being such that the distal end terminates at a point within a trachea when properly positioned;

a single inflatable cuff formed annularly around the outer surface of the primary tube proximate to the distal end;

a secondary flexible hollow tube having proximal and distal ends, the distal end terminating within the cuff, the proximal end extending out of the body of the patient and being adapted for attachment to cuff inflation means;

the cuff when inflated having an anterior surface oriented toward a bronchial tree of the patient, a superior surface oriented toward a larynx of the patient, and an outer surface which seals against an annular portion of the inner wall of the trachea, the superior surface of the cuff forming a cup having a rim extending furthermost up and toward the larynx, the bottom of the cup thereby forming a basin around the outer surface of the primary tube where it extends through the cuff; and a guide wire having proximal and distal ends, the distal end being attached at a point within the basin formed around the bottom of the cup formed in the cuff, the proximal end terminating freely outside a body of a patient, whereby an individual maintaining a patient may place a suction tube onto the proximal end of the guide wire and slide the suction tube therealong for precise placement into the basin to remove substances collected therein.

12. The endotracheal tube of claim 11, the proximal end of the primary tube further including means to releasably secure the proximal end of the guide wire when not in use.

\* \* \* \* \*